United States Patent [19]
Miller

[11] Patent Number: 5,220,689
[45] Date of Patent: Jun. 22, 1993

[54] SPORTGLASSES WITH CHEEK COVERING PORTIONS

[76] Inventor: Susan Miller, 275 Winwood Ave., Pacifica, Calif. 94044

[21] Appl. No.: 833,009

[22] Filed: Feb. 10, 1992

[51] Int. Cl.$^5$ .............................................. A61F 9/00
[52] U.S. Cl. ........................................ 2/12; 2/427; 351/44
[58] Field of Search ...................... 2/9, 11, 12, 15, 426, 2/427, 431, 432, 447, 448, 449; 128/858; 351/41, 44

[56] References Cited

U.S. PATENT DOCUMENTS

| | | | |
|---|---|---|---|
| D. 274,385 | 6/1984 | Newcomb | D2/234 |
| 1,799,064 | 3/1931 | Rickerd | 2/12 |
| 2,037,772 | 4/1936 | Everett et al. | 2/12 |
| 2,191,937 | 2/1940 | Low | 2/12 |
| 2,385,405 | 9/1945 | Crowther | 2/12 |
| 2,395,297 | 2/1946 | Shock, Jr. | 2/14 |
| 2,669,717 | 2/1954 | Diggs | 2/9 |
| 3,298,031 | 1/1967 | Morgan | 2/9 |
| 3,705,760 | 12/1972 | Langendorfer et al. | 351/44 |
| 4,515,448 | 5/1985 | Tackles | 351/44 |
| 4,541,125 | 9/1985 | Phillips | 2/10 |
| 4,621,378 | 11/1986 | Hatchman | 2/12 |
| 4,786,159 | 11/1988 | Piazza, Sr. et al. | 351/132 |
| 4,944,039 | 7/1990 | Dietrich | |
| 5,012,527 | 5/1991 | Michel | 2/9 |

Primary Examiner—Clifford D. Crowder
Assistant Examiner—Diana L. Biefeld
Attorney, Agent, or Firm—David Pressman

[57] ABSTRACT

A pair of sportglasses comprises a large, curved polymer lens (10) sized and shaped to shield the front and sides of the face from harmful solar radiation which may cause accelerated skin aging and skin cancer after repeated exposure. The lens has main portions (11) which cover the eyes (31) and cheeks (32), lower portions (13) which extend down the front of the face past the level of the mouth on either side to cover the side portions of the face (33), and rear portions (14) which wrap around the sides of the face to cover the sides of the face as far back as the ears. The large lens has an optical coating which significantly attenuates ultraviolet radiation, the most harmful component of sunlight, to protect most of the face from the damaging effects which may result after repeated exposure. A detachable nosepiece (19) protects the nose. The nostrils and mouth are left uncovered such that breathing and speaking are not impaired.

20 Claims, 2 Drawing Sheets

SPORTGLASSES WITH CHEEK COVERING PORTIONS

BACKGROUND

1. Field of Invention

This invention relates generally to protective devices for shielding the face from solar radiation, wind, snow, flying objects, caustic liquids, and other forces. Specifically, it relates to sportglasses which provide more effective protection against these forces.

2. Prior Art

Generations ago, suntans had a negative social image because they were obtained only by laborers who toiled outdoors. Avoiding the sun was therefore very important. Women wore wide hats and carried umbrellas to shield themselves from sunlight.

In the recent past, people became aware of the benefits of exercise. Those who played sports, such as football, and participated in aerobic activities, such as jogging, generally did so outdoors on sunny days. As a result, active and healthy people who exercised had tanned faces and bodies. For this reason, and because the affluent could afford vacation travel to sunbelt areas, suntans acquired a positive social image of good health and prosperity. Suntanning became extremely popular. People laid under the sun and even went to "tanning parlors" to get tanned without exercising.

However, in recent years the medical profession has determined that tanning may age skin prematurely and cause skin cancer, because the ultraviolet portion of sunlight is extremely damaging to living tissue. Thus the medical profession is now vigorously educating the public about the harmful effects of solar radiation. Accelerated skin aging manifests itself as discoloration, roughness, sagging, and wrinkling. Skin cancer, the most dangerous form of which is melanoma, is often fatal. These facts have greatly heightened people's awareness about the subject and seriously tarnished the image of the "perfect tan". Now, people, especially those with light complexions, generally seek protection from the sun.

Many products are available to help protect our faces from the sun's rays. Broad-brimmed hats can shield a face from overhead sunlight. However, they cannot prevent rays at a low angle from reaching the face. Furthermore, up to 85% of sunlight can be reflected onto a face from surfaces such as concrete, sand, snow, and water. In addition, carrying a wide hat can be very inconvenient. Therefore, the hat is inadequate because of its limited coverage, while its obtrusiveness tends to reduce people's unwillingness to use it.

Sunblock skin-lotions are more widely used to protect the skin from ultraviolet radiation. They can be applied to many parts of the body to provide maximum coverage. But sunblocks can be washed off by perspiration and be absorbed by the skin. Therefore, they are effective only for a limited amount of time, generally less than a few hours. They must be constantly reapplied to maintain protection and lotions with a higher SPF (Sun-Protection Factor) must be used. This inconvenience tends to reduce people's willingness to use the products. People with sun-sensitive skin often are also very sensitive to the chemicals that make up the sunblock lotions. As a result, sunblocks are ironically not a viable choice for the people who need protection the most. For example, the present patentee, who has a light complexion, was often sunburned from reflected light while wearing a hat and sportglasses and could not use sunscreen lotions because of allergies. Also, persons who have photo sensitive skin conditions, such as rosacea, lupus, polymorphous light eruption, and facial skin cancer, have no effective and practicable protective means available to shield their skins.

Perhaps the most popular form of facial sun protection is sportglasses. Common types are about the same size as prescription glasses. They are quite small and are extremely convenient to put on, remove, and carry. However, their convenient small size is also their greatest drawback because they protect just the eyes and the eyelids. Since many people often do not or cannot wear sunblock in addition to sportglasses, the rest of their faces are left exposed to harmful sunlight.

A number of attempts have been made to provide facial protection above that provided by ordinary sportglasses. U.S. Pat. No. 4,541,125 to Phillips (1985) shows eyeglasses which clip on to the underside of a cap visor. These glasses have relatively large lenses which provide coverage over the eyes and the cheeks. However, they still leave much of the face exposed. Moreover, they must be used with a cap.

U.S. Pat. Nos. 2,037,772 to Everett et al. (1936) and 4,786,159 to Piazza et al. (1988) show eyeglasses of average size with nosepieces which shield the nose. However, the extra coverage provided over simple sportglasses is minimal.

U.S. Pat. Nos. 2,385,405 to Crowther (1945), 2,395,297 to Shock (1946), 3,705,760 to Langendorfer et al. (1972), and 5,012,527 (1991) to Michel show goggles which are fitted closely with the face. They wrap around the eyes and cover the cheeks down to the level at about the base of the nose. Some cover the nose, while some do not, but all leave the sides or cheeks of the face exposed.

U.S. Pat. No. Des. 274,385 to Newcomb (1984) shows a face shield which attaches to ski goggles with hook-and-loop fasteners. The shield covers the nose, upper lip, and under part of the eyes, but not the cheeks. Because the shield must be used with ski goggles, it is not at all versatile.

U.S. Pat. Nos. 2,669,717 to Diggs (1954), 3,298,031 to Morgan (1967) and 4,944,039 to Dietrich (1990) show face shields with are attached to ordinary eye glasses. Intended for use in workshops or industrial situations for protection against flying debris or caustic liquids, the shields hang like curtains from the glasses to cover the whole front of the face down to the chin, but not the sides or cheeks. Because they cover the nose and mouth, they impair breathing and speaking. Therefore, they are practically and esthetically unsuitable for consumer applications.

All these devices either cover only the top half of the face such as the eyes, nose, and cheeks, or the whole front of the face down to the chin. Even with the devices which provide the greatest coverage, the sides or cheeks of the face are left uncovered. This exposes those areas to harmful ultraviolet radiation and its effects, such as accelerated skin aging and skin cancer. Moreover, those devices which cover the whole front of the face impair breathing and speaking.

OBJECTS AND ADVANTAGES

Accordingly, several objects and advantages of the invention are to provide a device which blocks harmful solar radiation from reaching the greatest area possible on the face, including the eyes, nose, and cheeks, yet which allows a user unobstructed vision, which leaves the nostrils and mouth uncovered for breathing and speaking, which is user customizable, which is shatter and scratch resistant, which is easy to don and remove, which does not irritate the skin, which does not fog up, and which is light and comfortable to wear.

Further objects and advantages will become apparent from the following description and the accompanying drawings.

DRAWING FIGURES

DRAWING REFERENCE NUMERALS

10: Lens
11: Main Portion
12: Bridge
13: Lower Portion
14: Rear portion
15: Temple Arm
16: Hinge
17: Screws
18: Trim piece
19: Nosepiece
20: Tab
21: Notch
22: Bridge Support
30: Wearer
31: Eyes
32: Cheek
33: Maxilla/Mandible Area

DESCRIPTION—FIG. 1

Figure 1:
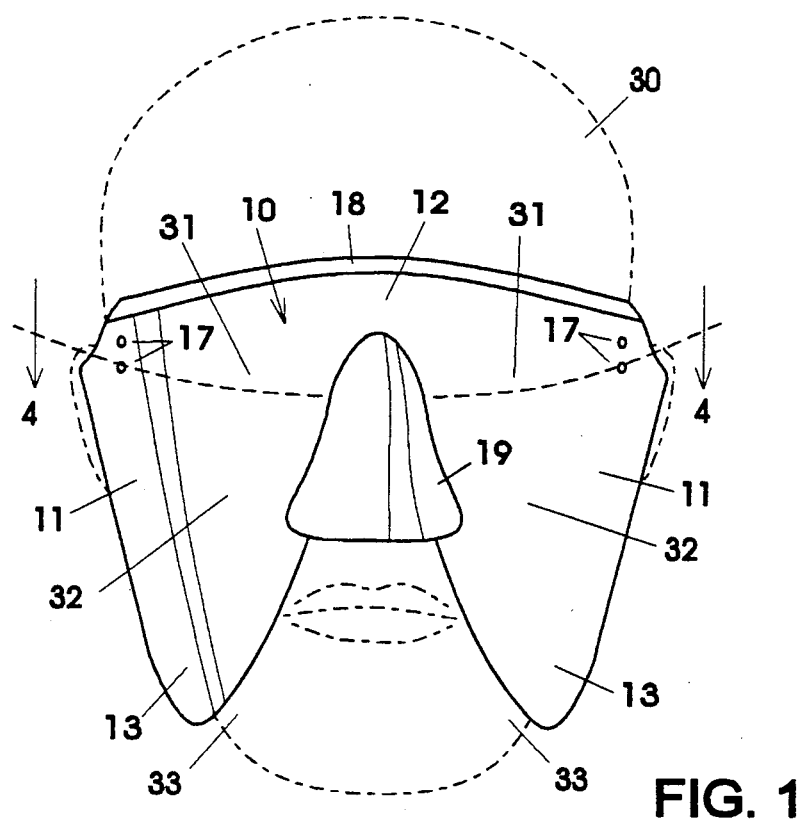
FIG. 1 is a front view of a pair of sportglasses in accordance with the invention.

In accordance with a preferred embodiment of the invention shown in FIG. 1, a pair of sportglasses has a large lens 10 for covering most of the face of wearer 30. Lens 10 provides maximum protection against harmful solar radiation, especially ultraviolet rays which can cause significant damage to living tissue after repeated exposure.

Lens 10 which is made of a single piece of brown tinted polycarbonate, sold under the trademark Lexan by General Electric Co. Polycarbonate is an extremely lightweight but shatter resistant material. The sheet used for lens 10 is covered with a well known type of coating that helps it to resist scratches.

Lens 10 has two distinct main portions 11 which are connected by a small bridge 12 at the upper center of the lens. Main portions 11, which are shaped roughly like butterfly wings, are curved to wrap around the front and sides of the face. Main portions 11 have lower portions 13 in the general shape of downward arches which extend far down over the cheeks of the face.

Positioned under bridge 12 is nosepiece 19, which curves around the front of the nose (not shown) to cover it but leaves the nostrils unobstructed. The inner edges of lower portions 13 and the bottom edge of nosepiece 19 form a trapezoidal open space in between so as to expose the nostrils for breathing, the mouth for breathing, eating, speaking, osculating, etc. A trim piece 18 borders the slightly curved top edge of lens 10, and extends between two pairs of screws 17.

Main portions 11 and lower portions 13 cover most of the front of the face, including eyes 31 (position indicated at the end of lead line), cheeks 32 (general position indicated at the end of lead line), and the jowls (outside portions of the maxilla and the upper portions of the mandible), indicated at 33. As stated, all of lens 10 is covered with a well known type of optical coating to significantly attenuate ultraviolet and infrared radiation, either direct or reflected from the ground, such that the shielded portions of the face are completely protected from all harmful effects of sunlight. Lens 10 is also tinted to reduce the intensity of transmitted visible light to improve eye comfort. Despite the unusually large area of coverage, the sportglasses do not impede breathing and speaking because, as stated, the open space between main portions 11 leaves the mouth and nostrils uncovered. Because the nostrils are exposed at the lower end of nosepiece 19, exhaled breath is free to escape. Therefore lens 10 does not fog. Due to the extremely large areas of main portions 11, all edges of lens 10 are positioned well away from the field of view of the eyes to provide unobstructed and undistorted vision. In addition, lens 10 is also large enough to protect the face from wind, snow, flying objects, caustic liquids, and a number of other forces.

DESCRIPTION—FIG. 2

Figure 2:
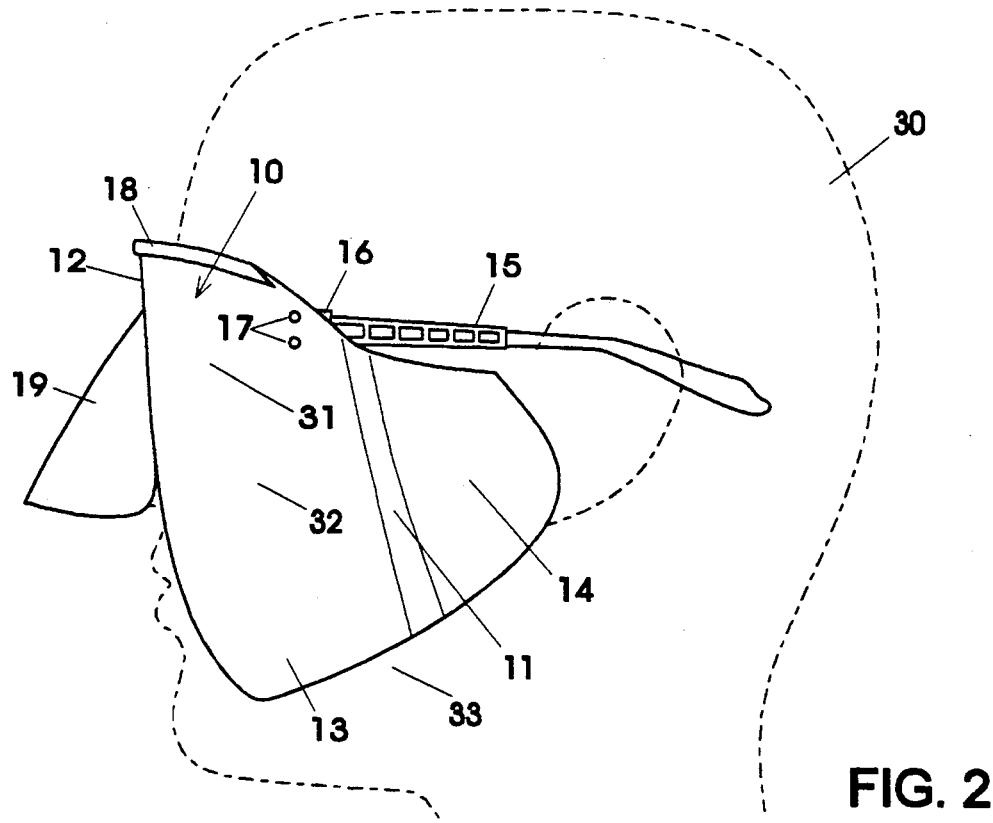
FIG. 2 is a left side view of the sportglasses of FIG. 1.
Figure 3:
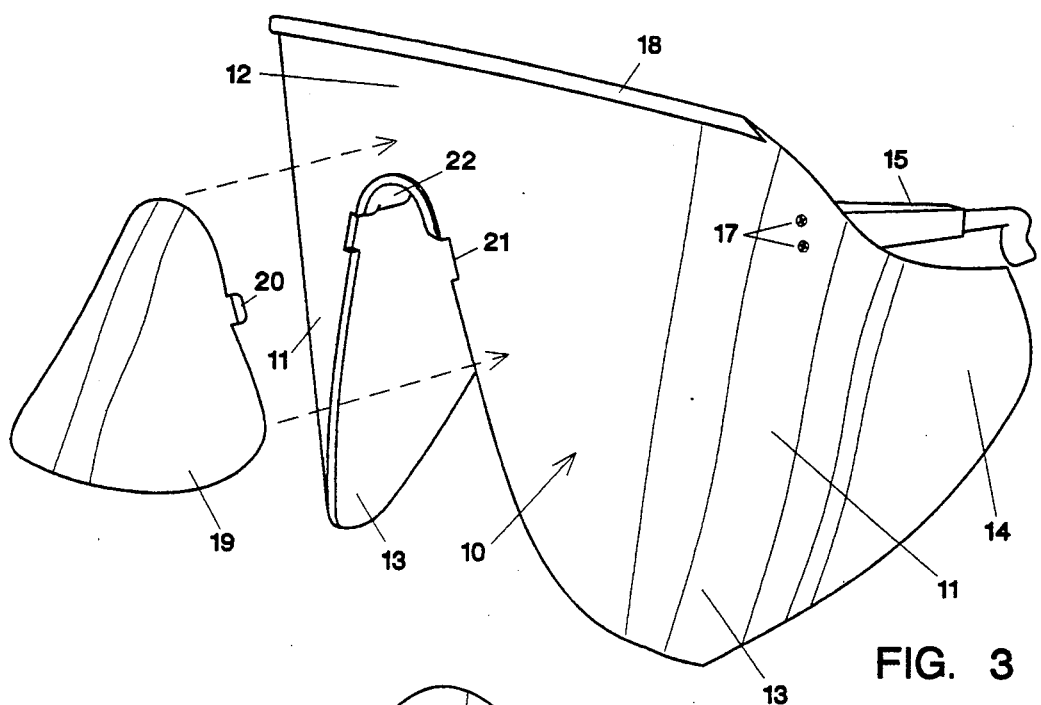
FIG. 3 is an exploded isometric view of the sportglasses of FIG. 1.
Figure 4:
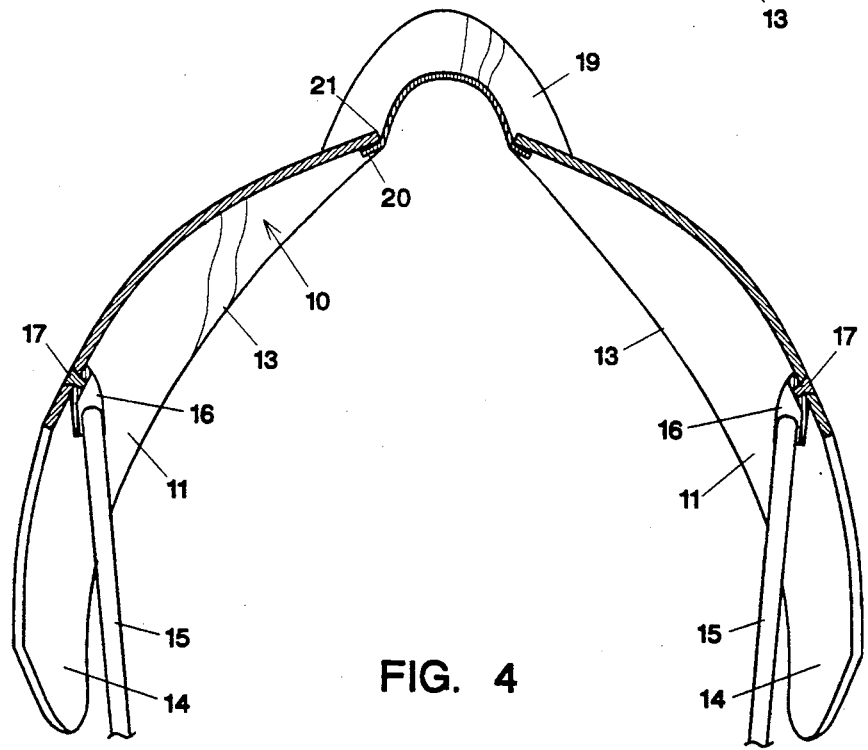
FIG. 4 is a top cutaway view of the sportglasses of FIG. 1. The view is taken as indicated by lines 4—4 of FIG. 1.

FIG. 2 is a left side view of the sportglasses of FIG. 1. The left and right sides of the sportglasses are symmetrical.

In addition to lower portion 13, main portion 11 also has a rearwardly extending portion 14 in the general shape of a sideways arch. The lower edge of main portion 11 sweeps upward from lower portion 13 to rear portion 14 in a curve which approximates the contour of the mandible. A conventional temple arm 15 is attached to hinge 16 which is fixed near the top of main portion 11 by a pair of screws 17. Nosepiece 19 has a triangular profile which approximates the profile of the nose underneath.

The area covered by main portion 11, lower portion 13, and rear portion 14 is large enough to completely shield eye 31, cheek 32, and jowl or maxilla/mandible area 33 from near the chin all the way back up to the ear. The nose is also completely covered by nosepiece 19, which extends from bridge 12 down past the bottom of the nose. As such, lens 10 is sized and shaped to shield an extremely large area of the face. Except for the mouth, which is left uncovered for ease of speaking, eating, etc, the whole of the face is completely protected by the coated lens 10 from the damaging rays of the sun, either direct or reflected from the ground. However, the sportglasses are attractive enough to be worn by consumers in public and in social gatherings.

Conventional temple arms 15 make the sportglasses extremely easy to don and remove, much like ordinary glasses. Lens 10 and nosepiece 19 are spaced away from the face to avoid any possible irritation, thereby comfort is maximized.

DESCRIPTION—FIG. 3

The sportglasses are made user customizable by nosepiece 19, which is detachable from lens 10. Two small rectangular tabs 20 (one shown) protrude from the midsides of nosepiece 19. Tabs 20 are folded outwardly about 50 degrees. Small, shallow notches 21 are formed on the inner edges of main portions 11 near bridge 12. Nosepiece 19 can be installed on the sportglasses by squeezing tabs 20 slightly towards each other to slip them between notches 21. Upon release, nosepiece 19 tends to resume its original shape, thereby urging tabs 20 against notches 21 to hold nosepiece 19 in place to protect the nose from sunlight. If desired, nosepiece 19 may be removed by squeezing its sides slightly inwardly to release tabs 20 from notches 21.

A nose bridge support 22 is attached to the top of the arch between main portions 11, directly under bridge 12. Bridge support 22 rests in the nasion and on the bridge of the nose to support the weight of lens 10. For maximum user comfort, bridge support 22 is made of a soft, rubbery material. The open arch shape of the front center portion of lens 10 is apparent in this figure.

DESCRIPTION—FIG. 4

Here the sportglasses are shown in a top sectional view. The curve of lens 10 is readily apparent, as is the significant reach backwards. Nosepiece 19 is also curved to fit around the front of the nose. Tabs 20 engage the back of main portions 11 behind notches 21. Temple arms 15 are connected to hinges 16. Hinges 16 have sharply angled front ends which are mounted to the inner surfaces at the sides of main portions 11 by screws 17. Temple arms 15 may be made adjustable in a number of ways by conventional means well known in the art.

In one embodiment lens 10 is 145 mm wide, 113 mm high, and curves back 115 mm.

SUMMARY, RAMIFICATIONS, AND SCOPE

Accordingly the reader will see that I have provided a greatly improved pair of sportglasses which employ jowl or cheek and maxilla/mandible area covering portions. They have an unusually large area and an ultraviolet and infrared attenuating coating to completely shield the eyes, nose, cheeks, and maxilla/mandible from the harmful solar radiation that may cause accelerated skin aging and fatal skin cancer. They are tinted to reduce the intensity of transmitted visible light to improve eye comfort. The large lens has an area which places all edges well away from the wearer's field of view to provide unobstructed and undistorted vision. Yet the glasses do not obstruct the nostrils or the mouth and is attractive enough to be worn in public or in social situations. They have a detachable nosepiece which allows the wearer to customize the sportglasses. They are made of materials which are shatter and scratch resistant. They use conventional temple arms which makes them extremely easy to don and remove. They are spaced away from the face such that they do not irritate the skin. They have a large, clear passage for exhaled breath so that the lens will not fog up. They are extremely light weight and therefore very comfortable to wear.

While the above descriptions are specific, they should not be construed as limitations on the scope of the invention, but only as examples of the preferred embodiment. Many other ramifications and variations are possible within the teachings of the invention. For example, different materials may be used for the lens and the coatings. The shape of the lens may be varied. The size of the lens may be increased to cover additional areas. The nosepiece may either be dispensed with or be non-removable. The tinting pattern may be varied. The temple arms may be adjustable. The two halves of the sportglasses may be hinged in the middle such that they may be folded. Prescription lenses may be incorporated by mounting them behind lens 10 or by incorporating them into lens 10, either integrally or as an installable.

Thus the reader is requested to determine the scope of the invention by the appended claims and legal equivalents, and not by the examples given.

I claim:

1. Sportglasses, comprising:
   a lens comprising a sheet curved to fit around the front and the sides of the face to shield the face from the harmful solar radiation which may cause accelerated skin aging and skin cancer, said lens having two distinct main portions sized and shaped to shield the eyes and the cheeks, said lens having an open space at a front center portion generally in the shape of an upward arch to leave the nose and mouth uncovered, said lens having lower portions on either side of said open space generally in the shape of downward arches which extend down to shield the side portions of the face to below the level of the mouth, said lens having rear portions generally in the shape of sideways arches which curve around sides of the face to extend generally back to the ears to shield the rear portions of the face, said lens having tinting to attenuate the intensity of transmitted visible light to improve eye comfort.

2. The sportglasses of claim 1, further including a nosepiece for shielding the front of the nose to shield the nose from harmful solar radiation.

3. The sportglasses of claim 2 wherein said nosepiece is detachable.

4. The sportglasses of claim 2, further including ultraviolet radiation attenuating means on the nosepiece for significantly attenuating the DB transmission of DB ultraviolet radiation to protect the nose from accelerated skin aging and skin cancer which may be caused by repeated exposure to ultraviolet radiation.

5. The sportglasses of claim 4 wherein said ultraviolet radiation attenuating means comprises a coating.

6. The sportglasses of claim 1, further including ultraviolet radiation attenuating means on said lens for significantly attenuating the transmission of ultraviolet radiation to protect the face from DB accelerated skin aging and skin cancer which may be caused by repeated exposure to ultraviolet radiation.

7. The sportglasses of claim 1, further including a nose bridge support attached to said front center portion of said lens and two hinged temple arms attached to said two main portions of said lens.

8. The sportglasses of claim 7 wherein said temple arms are adjustable.

9. Sportglasses, comprising:
   a lens comprising a polymer sheet curved to fit around the front and the sides of the face to shield the face from the harmful solar radiation which may cause accelerated skin aging and skin cancer, said lens having two distinct main portions sized and shaped to shield the eyes and the cheeks, said lens having an open space at a front center portion generally in the shape of an upward arch to leave the nose and mouth uncovered, said lens having lower portions on either side of said open space generally in the shape of downward arches which extend down to shield the side portions of the face to below the level of the mouth, said lens having rear portions generally in the shape of sideways arches which curve around the sides of the face to extend generally back to the ears to shield the rear portions of the face, said lens having tinting to attenuate the intensity of transmitted visible light to improve eye comfort, and ultraviolet radiation attenuating means on said lens for significantly attenuating the transmission of ultraviolet radiation to protect the face from accelerated skin aging and skin cancer which may be caused by repeated exposure to ultraviolet radiation.

10. The sportglasses of claim 9, further including a nosepiece for shielding the front of the nose to shield the nose from harmful solar radiation.

11. The sportglasses of claim 10 wherein said nosepiece is detachable.

12. The sportglasses of claim 10, further including ultraviolet radiation attenuating means on said nosepiece for significantly attenuating the transmission of ultraviolet solar radiation to protect the nose from accelerated skin aging and skin cancer which may be caused by repeated exposure to ultraviolet radiation.

13. The sportglasses of claim 9 wherein said ultraviolet radiation attenuating means comprises a coating.

14. The sportglasses of claim 9, further including a nose bridge support attached to said front center portion of said lens and two hinged temple arms attached to said two main portions of said lens.

15. The sportglasses of claim 14 wherein said temple arms are adjustable.

16. Sportglasses, comprising:
a lens comprising a polymer sheet curved to fit around the front and the sides of the face to shield the face from harmful solar radiation which may cause accelerated skin aging and skin cancer, said lens having two distinct main portions sized and shaped to shield the eyes and the cheeks, said lens having an open space at a front center portion generally in the shape of an upward arch to leave the nose and mouth uncovered, said lens having lower portions on either side of said open space generally in the shape of downward arches which extend down to shield the side portions of the face to below the level of the mouth, said lens having rear portions generally in the shape of sideways arches which curve around the sides of the face to extend generally back to the ears to shield the rear portions of the face, said lens having tinting to attenuate the intensity of transmitted visible light to improve eye comfort, a nosepiece for shielding the front of the nose to shield the nose from harmful solar radiation, said nosepiece being attached to said front center portion of said lens, ultraviolet radiation attenuating means on said lens and said nosepiece for significantly attenuating the transmission of ultraviolet radiation to protect the face from accelerated skin aging and skin cancer which may be caused by repeated exposure to ultraviolet radiation.

17. The sportglasses of claim 16 wherein said ultraviolet radiation attenuating means comprises a coating.

18. The sportglasses of claim 16 wherein said nosepiece is detachable.

19. The sportglasses of claim 16, further including a nose bridge support attached to said front center portion of said lens and two hinged temple arms attached to said two main portions of said lens.

20. The sportglasses of claim 19 wherein said temple arms are adjustable.

* * * * *

UNITED STATES PATENT AND TRADEMARK OFFICE
CERTIFICATE OF CORRECTION

PATENT NO. : 5,220,689
DATED : June 22, 1993
INVENTOR(S) : Susan Miller

It is certified that error appears in the above-indentified patent and that said Letters Patent is hereby corrected as shown below:

Column 6, Claim 4, line 3, delete "DB (both occurrences).

Column 6, Claim 6, line 4, delete "DB".

Signed and Sealed this

Eleventh Day of January, 1994

Attest:

BRUCE LEHMAN

*Attesting Officer*    *Commissioner of Patents and Trademarks*